United States Patent [19]

Bartman

[11] Patent Number: 5,037,402
[45] Date of Patent: Aug. 6, 1991

[54] DUAL-CHAMBER SAFETY SYRINGE

[76] Inventor: Thomas F. Bartman, 6601 Langdon. Ave., Van Nuys, Calif. 91406

[21] Appl. No.: 529,391

[22] Filed: May 29, 1990

[51] Int. Cl.⁵ .............................................. A61M 5/32
[52] U.S. Cl. .................................................... 604/198
[58] Field of Search ........................ 604/192, 197, 198

[56] References Cited

U.S. PATENT DOCUMENTS

| | | | |
|---|---|---|---|
| 3,822,701 | 7/1974 | Cloyd | 604/192 |
| 4,573,976 | 3/1986 | Sampson et al. | 604/198 |
| 4,723,943 | 2/1988 | Spencer | 604/198 |
| 4,850,961 | 7/1989 | Wanderer et al. | 604/198 |
| 4,915,696 | 4/1990 | Feimer | 604/198 |
| 4,932,947 | 6/1990 | Cardwell | 604/198 |
| 4,946,447 | 8/1990 | Hardcastle et al. | 604/198 |
| 4,978,344 | 12/1990 | Dombrowski et al. | 604/198 |
| 4,982,842 | 1/1991 | Hollister | 604/198 |

FOREIGN PATENT DOCUMENTS 8602715  5/1988  Netherlands ........................ 604/192

Primary Examiner—C. Fred Rosenbaum
Assistant Examiner—Sharon Rose
Attorney, Agent, or Firm—Michael A. Painter

[57] ABSTRACT

A hypodermic syringe incorporating a post-injection safety sheath for enclosing the sharpened needle tip. The hypodermic syringe incorporates parallel main and sheath chambers, the main chamber being to store fluid being injected or withdrawn, the parallel sheath chamber positioning the protective sheath. An axially aligned slot is disposed in the wall of the protective needle sheath and is aligned in communication with the ingress of the arcuate needle. A helical compression spring is coaxially aligned within the sheath chamber against the needle sheath biasing the sheath to enclosure the needle tip. When compressed, the needle sheath is withdrawn from the needle tip held in place through a detachable tab extending through the chamber wall.

9 Claims, 2 Drawing Sheets

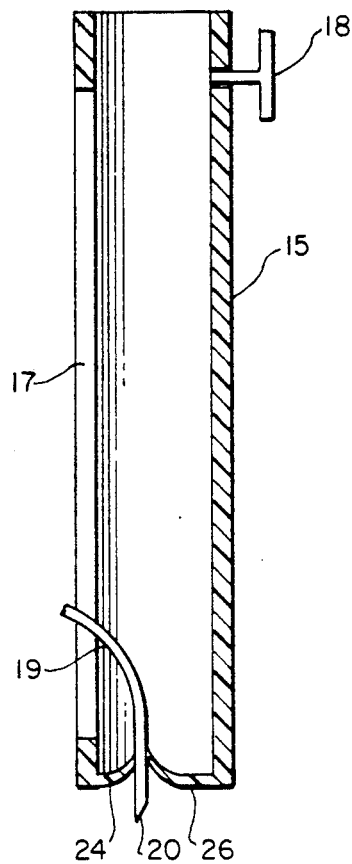
FIG. 5.
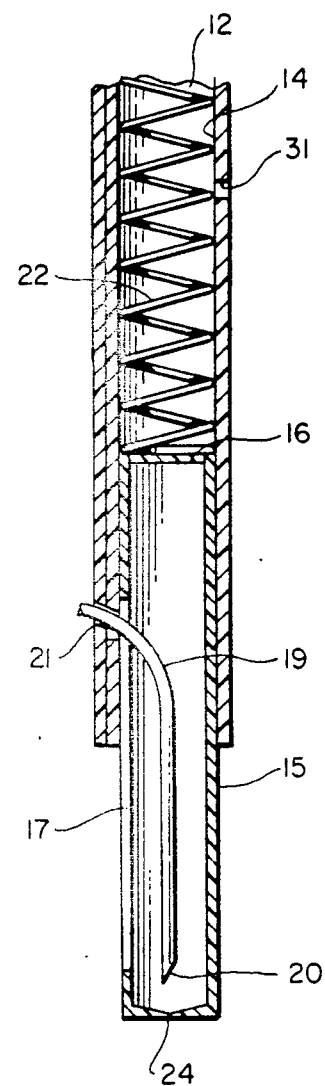
FIG. 6.
FIG. 7.
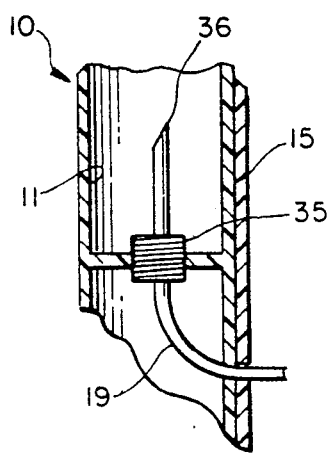

DUAL-CHAMBER SAFETY SYRINGE

BACKGROUND OF THE INVENTION

1. Field of the Invention

The present invention generally relates to devices used for the hypodermic injection of medication into or the withdrawal of fluid from a human patient, and more particularly, with a hypodermic syringe which employs a post-injection protective sheath about the needle tip.

2. Prior Art

The prior art discloses many devices for injecting medication into or withdrawing body fluids from human patients. Typically, devices taught by the prior art include syringes which receive measured quantities of medication to be injected or which can be used to draw samples of the patient's blood. Because these devices utilize injection needles, they are generally of a disposable nature and therefore discarded after a single use. Because of the risk of contamination, it is critical that individuals be protected from inadvertent contact with the needle tip after the hypodermic syringe has been used. This is particularly important when the needles have been applied to patients capable of contaminating the needles with blood-transmitted diseases such as hepatitis or acquired immune deficiency syndrome.

U.S. Pat. No. 4,804,371 is representative of the devices representing post-injection needle sheaths. The fluid chamber and the needle are in axial alignment. The device provides an assembly which employs a compression spring between the body of the needle and a protective cap. Prior to the injection, the distal end of the needle is disposed through an opening in the cap, the cap being in frictional engagement with the body holding the spring in a compressed position. After the injection, the cap is released thereby allowing the spring to extend. When the spring is in the extended condition, the distal end of the needle is misaligned with the opening in the cap so that the distal end is prevented from again passing through the opening in the cap.

The problems inherent in this device are representative of those which are exhibited in other devices which have sought to employ post-injection safety sheaths. The device contemplates that the spring will be in a compressed condition during use of the needle and until withdrawn from the patient. In substantially all devices disclosed by the prior art, the protective cap must be dislodged manually. Since the caps are generally maintained in place through a frictional fit, the user must employ both hands, one to hold the syringe, the other to release the protective cap. Since the protective sheaths are substantially adjacent the needle tips, the risk of accidental contact with the distal end of the needle is acute.

The present invention substantially resolves those problems inherent in the devices taught by the prior art. A hypodermic syringe constructed in accordance with the present invention employs a main chamber and an adjacent sheath chamber. The distal end of the hypodermic needle is in coaxial alignment with the sheath chamber, the opposite end being arcuately deflected and being in communication with the main chamber. This permits the present invention to be employed both for injecting medication into a patient and, with conventional modifications, for withdrawing blood from a patient. A protective sheath is slidably disposed within the sheath chamber, a helical spring being disposed between the top of the protective sheath and the chamber wall. When the spring is extended, the sheath will cover the distal end of the needle. In the compressed condition, the needle tip will be exposed for its intended use. A detachable tab extends outwardly from the wall of the protective sheath and through the wall of the sheath chamber in a location substantially away from the distal end of the needle. Either during or after the withdrawal of the needle, the exertion of manual force on the tab will detach the releasing tab thereby allowing the spring to extend thereby forcing the protective sheath about the distal end of the hypodermic needle.

SUMMARY OF THE INVENTION

The present invention comprises a disposable hypodermic syringe which incorporates a protective needle sheath. The syringe comprises a main storage chamber and a parallel sheath chamber. The dual-chamber syringe makes the present invention structure acceptable for both the injection of medication into a patient as well as the withdrawal of blood from a patient. The hypodermic needle is of an arcuate configuration, the distal end extending coaxially from the sheath chamber. The end opposite the distal tip of the needle is reinforced and extends through the common wall separating the main chamber from the sheath chamber and is communication with the main chamber. A protective sheath is slidably disposed within the sheath chamber. A slot is disposed through the wall of the sheath along its longitudinal axis and is disposed about the needle where the needle extends through the common wall between the main chamber and the sheath chamber. A helical compression spring is disposed within the sheath chamber adjacent the enclosed end of the protective sheath and biases the sheath to extend about the distal end of the needle. When the spring is compressed, a detachable tab extends outwardly from the outer surface of the protective sheath and through an aperture in the wall of the sheath chamber. When the detachable tab is broken, the spring will be allowed to extend forcing the sheath from the sheath chamber and closing the distal end of the needle.

It is therefore an object of the present invention to provide an improved hypodermic syringe incorporating a protective sheath.

It is another object of the present invention to provide a hypodermic syringe incorporating a protective sheath which can be used for both injecting medication and for withdrawing blood from the patient employing conventional vacuum evacuation tubes.

It is still another object of the present invention to provide a hypodermic syringe which incorporates a protective sheath which can be activated prior to the withdrawal of the needle from the patient.

It is still yet another object of the present invention to provide a hypodermic needle incorporating a protective sheath which is simple and inexpensive to fabricate.

The novel features which are believed to be characteristic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however, that the drawing is for the purpose of illustration and description only, and is not intended as a definition of the limits of the invention.

BRIEF DESCRIPTION OF THE DRAWING

FIG. 5 is an enlarged, cross-sectional view of the protective sheath and needle prior to use.

FIG. 6 is a side elevation, cross-sectional view of the present invention apparatus in an expanded condition, with the protective sheath enclosing the distal end of the needle.

FIG. 7 is a side elevation, partial cross-sectional view of the present invention syringe incorporating a coupling for conventional vacuum blood evacuation tubes.

DESCRIPTION OF THE PRESENTLY PREFERRED EMBODIMENT

Figure 1:
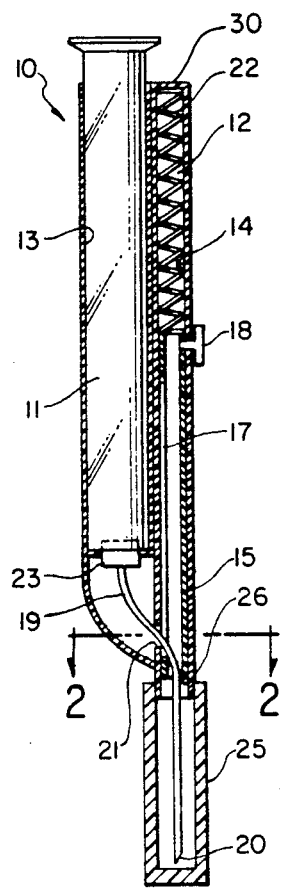
FIG. 1 is a side elevation, partial cross-section of a hypodermic syringe in accordance with the present invention.

An understanding of the present invention dual-chambered syringe can be best understood from FIG. 1 wherein a side elevation, partial cross-sectional view is shown, the syringe generally being designated by the reference numeral 10. Syringe 10 employs a main chamber 11 and a sheath chamber 12 which are disposed in parallel spaced relation to each other. Main chamber 11 is used to hold medication which is to be injected into the patient or, in an alternative embodiment, it can be employed to communicate with conventional vacuum blood evacuation tubes, the latter which will be described in detail hereinbelow. Main chamber 11 and sheath chamber 12 are cylindrical in profile, cylindrical wall 13 of main chamber 11 and cylindrical wall 14 of sheath chamber 12 being in communication only at needle aperture 21.

A hypodermic needle is generally provided with a conventional hub 23 which permits its connection to main chamber 11. Needle 19 employs arcuately deflected shank which extends through needle aperture 21 into the parallel sheath chamber 12. As can be best seen in FIG. 1 and FIG. 2, distal end 20 is coaxially aligned with sheath chamber 12. Prior to use, a standard needle shield or cap 25 is provided to cover the distal end 20 of needle 19. As stated, it is an objective of the present invention to permit its use with conventional vacuum blood evacuation tubes. The embodiment of the present invention syringe 10 shown in FIG. 1 employs a slider 9 which is conventionally used with hypodermic syringes when used to inject medication into a patient. In the embodiment shown in FIG. 7, injection needle 19 is provided with a hub 35 which includes an extension 36 thereof which can be coupled to conventional vacuum blood evacuation tubes.

Figure 2:
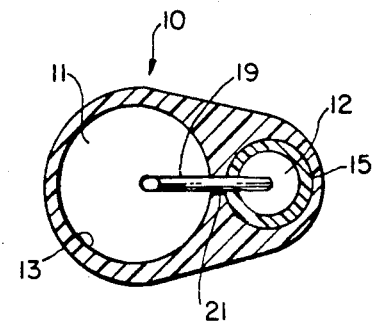
FIG. 2 is a cross-sectional view of the main chamber and sheath chamber of the hypodermic syringe shown in FIG. 1 taken through line 2—2 of FIG. 1.
Figure 3:
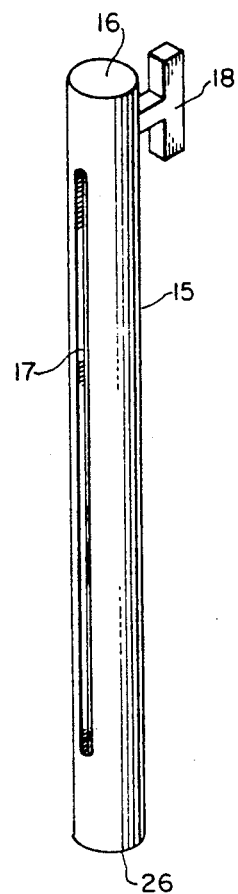
FIG. 3 is a perspective view of the needle protection sheath shown in FIG. 1.

As can be seen in FIG. 2, main chamber 11 and parallel sheath chamber 12 are cylindrical. It is understood that the geometric configuration of syringe 10 need only be sufficient to insure the integrity and alignment of main chamber 11 and sheath chamber 12, the shape thereof being merely one of choice. Protective sheath 15 is adapted to be coaxially disposed within sheath chamber 12 and to be moveable along their common longitudinal axis. The top end of protective sheath 15 is closed, the opposite end thereof being adapted to enclose the distal end 20 of the needle following use. This will be discussed in detail hereinbelow. Helical spring 22 is disposed within sheath chamber 12 intermediate sheath end 16 and the upper end 30 of sheath chamber 12. A longitudinal slot 17 is disposed through the cylindrical wall of protective sheath 15. When mounted within sheath chamber 12, slot 17 is aligned with needle aperture 21, needle 19 being disposed through slot 17, the distal end 20 of needle 19 being coaxially aligned with the longitudinal axis of protective sheath 15 and, prior to use, extending through protective end 26 of sheath 15.

Prior to use of syringe 10, protective sheath 15 is urged away from the distal end 20 of needle 19 compressing helical spring 22 between sheath end 16 and the top end 30 of sheath chamber 12. A detachable tab 18 is disposed through chamber wall aperture 31 and coupled to protective sheath 15. Tab 18 can be coupled to protective sheath 15 by aligning a mating aperture with wall aperture 31 or through the use of other conventional latches. As can be seen in FIG. 1, when spring 22 is in its compressed condition, the distal end 20 of needle 19 extends from the protective end 26 of sheath 15 thereby preparing syringe 10 for use. Protective end 26 can be best seen by reference to FIG. 5. Protective end 26 comprises a biased enclosure 24 having an aperture centrally disposed therethrough which is aligned with distal end 20 of needle 19. When protective sheath 15 compresses helical spring 22, distal end 20 projects through the aperture in biased enclosure 24 preparing syringe 10 for use.

As stated, a primary objective of the present invention is to permit the activation of protective sheath 15 without placing the user in proximity to the distal end 20 of needle 19. Activating protective sheath 15 requires only the removal of tab 18 from aligned apertures 31 and 32 in syringe body 10 and protective sheath 15, respectively. Protective sheath 15 will place spring 22 in its compressed condition only so long as tab 18 remains in place. Once tab 18 is disengaged, helical spring 22 will extend along the longitudinal axis of sheath chamber 12 thereby causing protective sheath 15 to be urged toward distal end 20 of needle 19. Since needle 19 is disposed within slot 17, sheath 15 remains in axial alignment with needle 19. In its extended condition, the protective end 26 of sheath 15 will travel beyond needle tip 20 upon which the biased enclosure 24 will prevent later inadvertent contact with needle tip 20.

Figure 4:
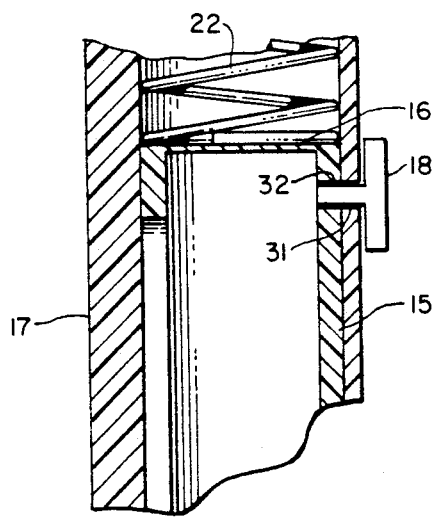
FIG. 4 is an enlarged, fragmentary, cross-sectional view of the protective sheath shown in its pre-injection condition.
Figure 8:
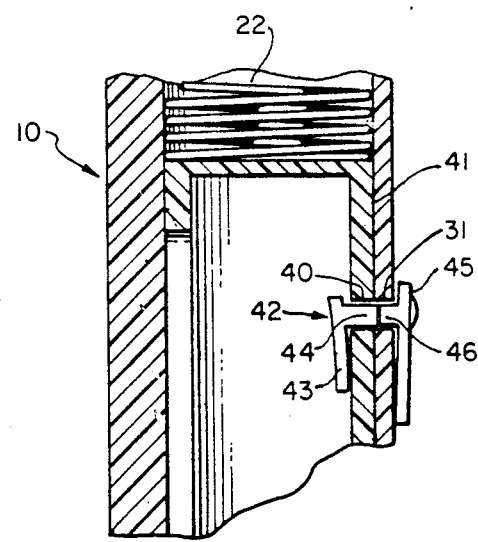
FIG. 8 is a side elevation, partial cross-sectional view of the present invention dual-chambered syringe employing an alternative embodiment for the protective sheath and release mechanism.

An alternative embodiment which may be employed to implement the structure necessary to activate protective sheath 41 can be best seen by reference to FIG. 8. As with the embodiment shown in FIG. 4, an aperture 31 is disposed through the wall of syringe 10 and is adapted to be aligned with an aperture 40 in an alternative embodiment of protective sheath 41. A biased catch 42 is adapted to maintain protective sheath 41 in place and compress helical spring 22 prior to activation. Catch 42 consists of a biased flange 43 which is secured at one end thereof to the interior wall of protective sheath 42, the other end having extending therefrom a projection 44 which extends into apertures 31 and 40 adapted to maintain the alignment between protective sheath 41 and the body of syringe 10 prior to use. The protective sheath 41 is activated by depressing latch 45. Since pin 46 is in axial abutment with projection 44, depressing latch 45 causes projection 44 to be internally withdrawn from aperture 31 thereby allowing helical spring to move to its extended position urging protective sheath 15 toward the distal end 20 of injection needle 19.

It can therefore be seen the primary objectives of the present invention are achieved through the use of the dual-chambered syringe. Prior to and during use of the syringe, one has a clear and unobstructed view of the entry point. Most importantly, the needle tip 20 can be enclosed within protective sheath 15 either during use or after withdrawal of needle tip 20 by removal of tab 18 which causes spring 22 to extend thereby urging protective tip 26 of sheath 15 axially beyond needle tip 20.

I claim:

1. A hypodermic syringe including a protective sheath for enclosing the distal end of a needle comprising:
   (a) a syringe body having a cylindrical main chamber and a cylindrical sheath chamber, said main chamber and sheath chamber being in parallel spaced relation to each other, a needle channel being disposed through the syringe body intermediate the main chamber and sheath chamber at one end thereof;
   (b) an injection needle including a chamber hub, an arcuate shank and a distal end, the chamber hub being coupled to the main chamber, the arcuate shank being disposed through the needle channel and being in communication with said sheath chamber, said distal end being axially aligned with and extending from said sheath chamber;
   (c) a protective sheath axially disposed within said sheath chamber, said protective sheath being defined by a cylindrical wall and having an upper enclosed end and a lower protective sleeve means for enclosing the distal end of the injection needle and a slot longitudinally disposed through said cylindrical wall and through which the arcuate shank of said injection needle is disposed;
   (d) biasing means disposed within said sheath chamber for providing a force to urge said protective sheath toward the distal end of said injection needle; and
   (e) compression release means for limiting the movement of said protective sheath toward the distal end of said injection needle coupled intermediate said protective sheath and said syringe body.

2. A hypodermic syringe as defined in claim 1 wherein said chamber hub includes means for communicating with a vacuum blood evacuation tube.

3. A hypodermic syringe as defined in claim 1 wherein said biasing means is a helical means.

4. A hypodermic syringe as defined in claim 3 wherein said compression release means comprises a detachable release tab removeably disposed through the syringe body and coupled to said protective sheath whereby said helical spring is maintained in a compressed state.

5. A hypodermic syringe as defined in claim 3 wherein said compression release means comprises a biased member secured to the inner cylindrical wall of said protective sheath, a projection extending radially outwardly therefrom and movably disposed through an aperture formed in said cylindrical wall and syringe body, and activation means for depressing said projection coupled to the syringe body.

6. A hypodermic syringe as defined in claim 1 wherein said protective sleeve means comprises a resilient end having an aperture disposed therethrough which slidably engages the distal end of said injection needle when said biasing means is in a compressed state and which is adapted to enclose the distal end of said needle when said biasing means is extended.

7. A hypodermic syringe incorporating a protective needle sheath comprising:
   (a) a syringe body having a main chamber and sheath chamber in parallel spaced relation to each other, said main chamber and sheath chamber being separated by an internal wall of said syringe body and being in communication with each other through a needle channel disposed in said internal wall;
   (b) an injection needle including a main chamber hub, an arcuate shank and a sharpened distal end, the main chamber hub being axially aligned with and coupled to the main chamber, the arcuate shank being secured within the needle channel and extending into and being in communication with said sheath chamber, the sharpened distal end being coaxially aligned within and extending from said sheath chamber;
   (c) a cylindrical sheath slidably disposed within said sheath chamber and having a rearward enclosed end and a forward end, a longitudinal slot being disposed through the cylindrical wall which is aligned with the needle aperture disposed through the internal wall of said syringe body and within which the arcuate shank of said injection needle is slidably disposed, the forward end of said protective sheath being adapted to circumscribe the sharpened distal end of said injection needle;
   (d) a helical spring disposed within the sheath chamber and being adjacent the rearward end of said protective sheath biasing said protective sheath towards the sharpened distal end of said injection needle; and
   (e) a detachable locking tab coupling said protective sheath to said syringe body and to maintain the helical spring in a compressed position whereby the sharpened distal end of said injection needle will be enclosed upon the removal of said locking tab.

8. A hypodermic syringe as defined in claim 7 wherein said protective sheath further includes at the forward end thereof a resilient sleeve having an aperture disposed therethrough which slidably engages the sharpened distal end of said injection needle when said helical spring is in a compressed state and which is adapted to enclose the distal end of said injection needle when said helical spring is extended.

9. A hypodermic syringe as defined in claim 7 wherein said main chamber hub includes means for communicating with a vacuum blood evacuation tube.

* * * * *